United States Patent
Chow et al.

(10) Patent No.: US 9,913,986 B2
(45) Date of Patent: Mar. 13, 2018

(54) IMPLANTABLE MEDICAL DEVICE SWITCH MATRIX

(71) Applicant: CYBERONICS, INC., Houston, TX (US)

(72) Inventors: Eric Y. Chow, Houston, TX (US); David L. Thompson, Houston, TX (US)

(73) Assignee: Cyberonics, Inc., Houston, TX (US)

(*) Notice: Subject to any disclaimer, the term of this patent is extended or adjusted under 35 U.S.C. 154(b) by 467 days.

(21) Appl. No.: 13/741,205

(22) Filed: Jan. 14, 2013

(65) Prior Publication Data

US 2014/0200638 A1  Jul. 17, 2014

(51) Int. Cl.
| | |
|---|---|
| *A61N 1/00* | (2006.01) |
| *A61N 1/36* | (2006.01) |
| *A61N 1/08* | (2006.01) |
| *A61N 1/14* | (2006.01) |
| *A61N 1/05* | (2006.01) |
| *A61N 1/39* | (2006.01) |
| *A61N 1/37* | (2006.01) |

(52) U.S. Cl.
CPC ..... *A61N 1/36125* (2013.01); *A61N 1/36142* (2013.01); *A61N 1/05* (2013.01); *A61N 1/08* (2013.01); *A61N 1/14* (2013.01); *A61N 1/3718* (2013.01); *A61N 1/3912* (2013.01)

(58) Field of Classification Search
CPC ... A61N 1/05; A61N 1/08; A61N 1/14; A61N 1/36125; A61N 1/3912; A61N 1/36142; A61N 61/36125; A61N 1/3718
USPC ............ 607/1, 2, 6, 9, 30, 32, 34, 37
See application file for complete search history.

(56) References Cited

U.S. PATENT DOCUMENTS

| | | | |
|---|---|---|---|
| 4,726,379 A | | 2/1988 | Altman et al. |
| 5,431,692 A | * | 7/1995 | Hansen et al. ................. 607/28 |
| 5,472,454 A | * | 12/1995 | Ozawa .............................. 607/5 |
| 5,522,856 A | * | 6/1996 | Reineman ......................... 607/9 |
| 6,035,237 A | | 3/2000 | Schulman et al. |
| 7,532,936 B2 | | 5/2009 | Erickson et al. |
| 7,555,345 B2 | | 6/2009 | Wahlstrand et al. |
| 7,822,482 B2 | | 10/2010 | Gerber |
| 7,962,224 B1 | | 6/2011 | Blischak |
| 2003/0149456 A1 | * | 8/2003 | Rottenberg et al. ............ 607/37 |
| 2004/0088012 A1 | * | 5/2004 | Kroll et al. ........................ 607/9 |
| 2004/0210255 A1 | * | 10/2004 | Degroot et al. .................. 607/5 |
| 2007/0255335 A1 | | 11/2007 | Herbert et al. |
| 2008/0249584 A1 | | 10/2008 | Scheurer |
| 2009/0005833 A1 | | 1/2009 | Cameron et al. |
| 2009/0112292 A1 | * | 4/2009 | Armstrong ...................... 607/63 |
| 2011/0245888 A1 | * | 10/2011 | Badelt et al. ..................... 607/6 |

* cited by examiner

*Primary Examiner* — Lindsey G Wehrheim
(74) *Attorney, Agent, or Firm* — Foley & Lardner LLP

(57) ABSTRACT

A particular implantable device includes one or more electrode connectors and multiple circuit elements within a housing. The implantable medical device may also include one or more switches, where each switch of the one or more switches is coupled between one or more of the multiple circuit elements and at least one electrode connector of the one or more electrode connectors.

20 Claims, 8 Drawing Sheets

IMPLANTABLE MEDICAL DEVICE SWITCH MATRIX

FIELD OF THE DISCLOSURE

The present disclosure is generally related to a switch matrix of an implantable medical device.

BACKGROUND

Implantable medical devices are used for a variety of medical purposes including treatment of particular medical conditions, gathering patient body parameter data, and providing regular doses of therapy such as electro-stimulation or medications. Such implantable medical devices may include internal circuitry coupled to one or more external electrodes or electrode connectors. Electrostatic discharge during handling of such implantable medical devices can cause damage to internal electronics. Such damage to an implantable medical device may remain unnoticed until after the implantable medical device is implanted within a patient. If the electrostatic discharged caused significant damage to the implantable medical device, the implantable medical device may have to be removed via a subsequent medical procedure, at significant cost and inconvenience, as well as additional risk to the patient.

SUMMARY

In a particular embodiment, an implantable medical device includes a switch matrix. One or more switches of the switch matrix may be electrically coupled between an external electrode connection of the implantable medical device and internal circuitry of the implantable medical device. Accordingly, when a particular switch of the switch matrix is open, a corresponding electrode connection of the implantable medical device may be decoupled from the internal circuitry. Conversely, when the particular switch is closed, the corresponding electrode connection may be coupled to the internal circuitry. Thus, the switch matrix may provide electrostatic discharge protection to the internal circuitry when one or more switches of the switch matrix are open and may provide operational coupling of the external electrode connections to the internal circuitry when the one or more switches are closed.

In a particular embodiment, an implantable medical device may have multiple operational modes. For example, the operational modes may include a treatment mode, a sensing mode, a charging mode (e.g., inductive or far-field radiative charging signals), an RF communication mode, a magnetic resonance imaging (MRI) mode, other modes, or a combination thereof. For charging mode, RF communication mode, or MRI mode it may be beneficial to open one or more of the switches of the switch matrix to disconnect the leads to reduce the amount of noise and energy transferred from the leads to the circuitry or circuitry to the leads and electrodes. In the treatment mode, therapeutic treatment, such as medication or stimulation may be provided to target tissue of the patient. When the therapeutic treatment includes electrical stimulation, one or more of the electrode connections may be used to provide a stimulation signal (e.g., a current) to the target tissue of the patient. In the sensing mode, one or more of the electrode connections may be used to gather body parameter data of the patient. In this embodiment, the one or more switches may be configured to provide other benefits or operational functions in addition to or instead of electrostatic discharge protection. For example, one or more switches of the switch matrix may be opened during a treatment mode to prevent current from passing through a particular electrode connection in an unintended manner (e.g., a leakage current). One or more switches of the switch matrix may be opened during sensing in the sensing mode.

In a particular embodiment, one or more switches of the switch matrix may be controllable remotely via a signal sent from an external device. In this embodiment, the implantable medical device can be placed in a safe mode (e.g. an implantation mode), during implantation of the implantable medical device. For example, in the safe mode, one or more switches of the switch matrix may be open to protect the implantable medical device from electrostatic discharge. The implantable medical device can be switched to an operational mode via a signal transmitted from an external device after implantation of the implantable medical device. In the operational mode, particular switches of the switch matrix may be closed to connect the external electrode connectors to the internal circuitry of the implantable medical device.

In a particular embodiment, an implantable medical device may include a housing, one or more electrode connectors, and multiple circuit elements within the housing. The implantable medical device may also include one or more switches within the housing, where each switch of the one or more switches is coupled between one or more of the multiple circuit elements and at least one electrode connector of the one or more electrode connectors.

In a particular embodiment, a method includes, after implantation of an implantable medical device in a patient, transmitting an activation signal to the implantable medical device. In response to the activation signal, the implantable medical device changes modes from an implantation mode to an operational mode by closing one or more switches within a housing of the implantable medical device. Each switch of the one or more switches is coupled between one or more of multiple circuit elements within the housing and at least one electrode connector.

In a particular embodiment, a method includes closing a first switch when a first operational mode of an implantable medical device is selected. The first switch is located in a circuit path between a housing of the implantable medical device and one or more circuit elements within the implantable medical device. The method also includes gathering body parameter data, in the first operational mode, by using the housing as an electrode. The method further includes opening the switch when a second operational mode of the implantable medical device is selected, and applying an electrical signal generated by a stimulation circuit of the implantable medical device to tissue of a patient via electrodes coupled to the stimulation circuit via one or more electrode connectors.

The features, functions, and advantages that have been described can be achieved independently in various embodiments or may be combined in yet other embodiments, further details of which are disclosed with reference to the following description and drawings.

DETAILED DESCRIPTION

Figure 1:
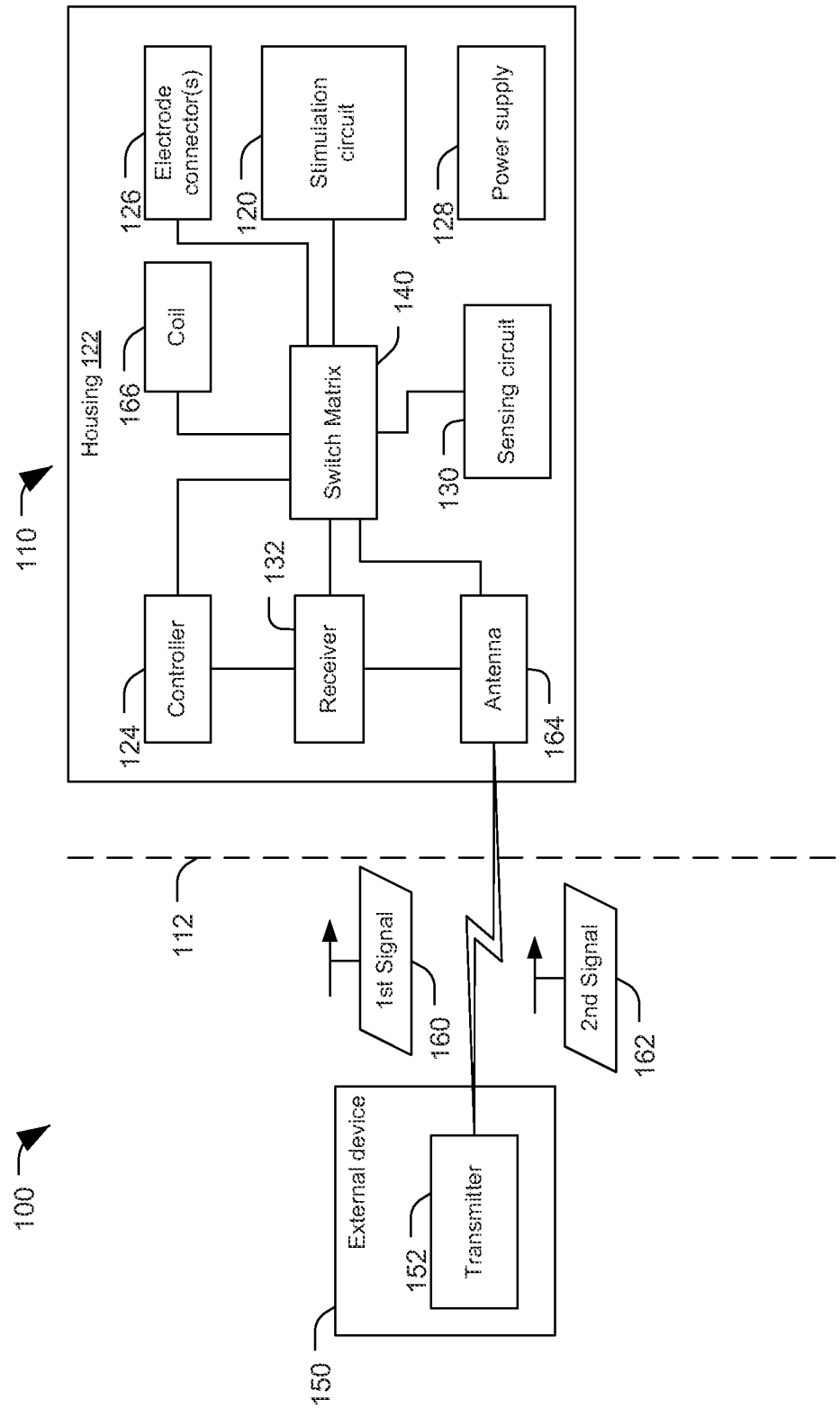
FIG. 1 is a block diagram of a particular embodiment of a system including an implantable medical device and an external device.

FIG. 1 is a block diagram of a particular embodiment of a system 100 including an implantable medical device 110 and an external device 150. The implantable medical device 110 includes multiple circuit elements within a housing 122. The multiple circuit elements may include a stimulation circuit 120 that is configured to generate electrical stimulation signals to be provided to target tissue of a patient via one or more electrode connectors 126. The multiple circuit elements may include a sensing circuit 130 that is configured to sense body parameter data from tissue of the patient via one or more of the electrode connectors 126.

The implantable medical device 110 may also include a power supply 128, such as a battery, a capacitor, an ultra capacitor, another charge storage element, or another power source. In a particular embodiment, the implantable medical device 110 includes a controller 124. The controller 124 may be operable to control other elements or functional modules of the implantable medical device 110, such as the stimulation circuit 120, the sensing circuit 130 and a receiver 132. In a particular embodiment, the controller 124 is responsive to the receiver 132 to provide control signals to other circuit elements or functional modules of the implantable medical device 110 (e.g., responsive to a first signal 160 received from the external device 150). The controller 124 may include a processor, an application specific integrated circuit (ASIC), a memory including instructions executable by a processor of the implantable medical device 110, or a combination thereof.

In a particular embodiment, the implantable medical device 110 includes a switch matrix 140 (such as one or more electromechanical switches, multiple electromechanical switches in a single package (e.g., an array of switches), or switched integrated onto an ASIC platform). The switch matrix 140 may be coupled to one or more circuit elements of the implantable medical device 110. For example, the switch matrix 140 may be coupled between one or more of the electrode connectors 126 and one or more other circuit elements, such as the stimulation circuit 120, the sensing circuit 130, the controller 124, the receiver 132, the power supply 128, the receiver 132, the antenna 164, the coil 166 (used for recharge and/or communication), the housing 122 or other components of the implantable medical device 110. The switch matrix 140 includes one or more switches. The switch matrix 140 may be responsive to commands received from the controller 124, commands received from the receiver 132, or both.

In a particular embodiment, the switch matrix 140 is operable to change a circuit path configuration of the implantable medical device 110 based on a mode of operation of the implantable medical device 110. For example, the implantable medical device 110 may be operable in multiple modes, such as an implantation mode (or safe mode) and one or more operational modes. The operational modes may include, for example, a stimulation mode, a sensing mode, a recharge mode, a communication mode, and an MRI (magnetic resonance imaging) mode.

The switch matrix 140 may open particular switches, close particular switches, or open some switches and close other switches when the implantable medical device 110 changes from one operational mode to another operational mode. For example, to enter the implantation mode, the switch matrix 140 may open multiple switches, such as each switch coupled between one of the electrode connectors 126 and another element of the implantable medical device 110. To illustrate, the switch matrix 140 may open every switch that is coupled to one of the electrode connectors 126 or to the housing 122 when the implantable medical device 110 enters the implantation mode. As another example, when the implantable medical device 110 enters the stimulation mode, the switch matrix 140 may close one or more switches in connections between the stimulation circuit 120 and the electrode connectors 126. Additionally or in the alternative, the switch matrix 140 may open one or more switches to disable electrical connections between the electrode connector 126 and the sensing circuit 130. In yet another example, when the implantable medical device 110 enters the sensing mode, the switch matrix 140 may open one or more switches between the stimulation circuit 120 and the electrode connectors 126 and may close one or more switches between the sensing circuit 130 and the one or more electrode connectors 126.

In operation, the implantable medical device 110 may be placed in the implantation mode prior to implantation of the implantable medical device 110 in a patient 112. For example, a transmitter 152 of the external device 150 may send a first signal 160 (e.g., a message sent via wireless transmission, such as via a propagating electromagnetic wave) to the implantable medical device 110, which may be received by the receiver 132. In response to the first signal 160, the receiver 132 or the controller 124 may cause the switch matrix 140 to open one or more switches to disable electrical connections between the electrode connectors 126 and other circuit elements of the implantable medical device 110. Accordingly, the implantable medical device 110 may be protected against electrostatic discharge at the housing, at one or more electrode connectors, or both.

After implantation of the implantable medical device 110, within the patient 112, the external device 150 may be used to send a second signal 162 (e.g., a second message sent via wireless transmission, such as via a propagating electromagnetic wave) to the implantable medical device 110, which may be received by the receiver 132. In response to the second signal 162, the receiver 132 or the controller 124 may cause the switch matrix 140 to change the position of one or more switches of the switch matrix 140. In a particular embodiment, in response to the second signal 162, the controller 124 may select and activate one or more operational modes of the implantable medical device 110. For example, the controller 124 may include operational instructions, such as a treatment plan, a data gathering plan, or both, that specify when the implantable medical device 110 is to operate in particular operational modes. To illustrate, the implantable medical device 110 may normally operate in the stimulation mode and may periodically or occasionally change to the sensing mode (e.g., based on occurrence of an event, such as expiration of a time period). Alternately, the implantable medical device 110 may normally operate in the sensing mode and may periodically or occasionally change to the stimulation mode. In yet another example, the implantable medical device 110 may alternate operation between the stimulation mode and the sensing mode. In still another example, the second signal 162 may specify operation of the implantable medical device 110 in a particular operational mode, such as the stimulation mode or the sensing mode. In this example, the implantable medical device may operate in the specified operational mode until a subsequent signal is received from the external device 150 or until the controller 124 determines to change the operational mode based on the treatment plan, the sensing plan, or another overriding instruction.

In a particular embodiment, the housing 122 may be used as a sensing electrode by the sensing circuit 130. In this embodiment, when stimulation is provided by the stimulation circuit 120, leakage current may pass to the housing 122 providing unintended electrical signals to tissue of the patient that is not target tissue and/or causing heating of the housing 122 through current dissipation. Accordingly, to address this concern, when the stimulation mode is selected, the controller 124 may cause the switch matrix 140 to open a switch between the housing 122 and the stimulation circuit 120. Opening the switch may prevent or reduce stimulation current from leaking to the housing. In stimulation mode, the switches of the switch matrix 140 associated with the coil 166, the antenna 164, the receiver 132, or a combination thereof, may be opened to minimize energy transferred from these components to the housing 122, the electrode connector(s) 126, the stimulation circuit 120, or other electrical components of the implantable medical device. The switch matrix 140 may also be used to short two or more stimulation circuit 120 outputs after delivering a stimulation pulse to ensure charge balancing. The switch matrix 140 may also be used to drain charge build up on the housing 122 or leads connected to the electrode connector(s) 126. The switch matrix 140 may also be used to reverse the polarity of the electrodes used to deliver the stimulation pulse When the sensing mode is selected, the controller 124 may cause the switch matrix 140 to close a switch between the sensing circuit 130 and the housing 122. Accordingly, the sensing circuit 130 can use the housing 122 as a sensing element or a sensing electrode in order to gather body parameter data. In sensing mode, the switches of the switch matrix 140 associated with the coil 166, the antenna 164, the receiver 132, or a combination thereof, may be opened to minimize energy transferred from these components to the housing 122, the electrode connector(s) 126, the sensing circuit 130, or other electrical components of the implantable medical device. Opening the switches associated with the coil 166, the antenna 164, the receiver, or a combination thereof, may improve the performance of the sensing circuit 130.

In particular embodiments, the implantable medical device 110 includes one or more additional components. For example, the implantable medical device 110 may include a memory to store body parameter data gathered by the sensing circuit 130. In another example, the implantable medical device 110 may include a transmitter or transceiver in order to transmit body parameter data gathered by the sensing circuit 130 to the external device 150 or to another external device.

Additionally or in the alternative, the power supply 128 may be a rechargeable power supply that is recharged responsive to a charging signal from the external device 150 or another external device. In this embodiment, the controller 124 may include instructions to select a charging mode of the implantable medical device 110. In the charging mode of the implantable medical device 110, the controller 124 may cause the switch matrix 140 to select particular positions for one or more switches of the switch matrix 140. For example, the switch matrix 140 may open one or more switches coupled to the electrode connectors 126, the housing 122 or both, in order to mitigate a risk of the charging signal causing unintended current flow through the housing or electrode connectors 126. In addition, switches associated with the sensing circuit 130 and/or the stimulation circuit 120 may be closed to prevent damage to circuit components. In another example, the switch matrix 140 may close one or more switches in order to enable charging of the power supply 128. For example, the switch matrix 140 may close one or more switches associated with the coil 166 (e.g., a recharge coil) to permit the coil 166 to transfer power received from an external coil (not shown) to the power supply 128. One or more switches associated with the antenna 164 and/or the receiver 132 may also be closed during the recharge process or at various times during the recharge process to provide feedback and status communication to circuitry operating the external coil. One or more switches associated with the sensing circuit 130, the stimulation circuit 120, and the electrode connector(s) 126 may also be opened during the recharge process or at various times during the recharge process to protect the circuitry and the patient from coupled energy. Switches, or a portion of the switches, associated with the sensing circuit 130 may be closed during charging, however, the thresholds for detecting an event and/or filter settings may be adjusted in some fashion to account for the noise injected from the charging signal. If charging time overlaps with a scheduled therapy or therapy in response to a detected event, the switch matrix 140 may be configured to close the appropriate switches to allow electrical stimulation. In another example, the antenna 164 may be configured to receive far-field RF powering signals to recharge the power supply 128. In this example, one or more switches associated with the antenna 164 may be closed to permit charging.

In a particular embodiment, the implantable medical device 110 may be exposed to high power electromagnetic energy during, for example, an MRI procedure. The implantable medical device 110 may include an MRI mode in which one or more of the switches of the switch matrix 140 are placed in an open position to protect the circuitry and the patient from coupled energy. The switch matrix 140 may be configured to open one or more switches corresponding to the housing 122, the electrode connector(s) 126, the sensing circuit 130, the antenna 164, the receiver 132, the coil 166, the stimulation circuit 120, the controller 124, or a combination thereof. The MRI mode may be entered onto in response to a user input via the external device 150, a magnet swipe or tap at the implantable medical device 110, or in response to detection of the high power electromagnetic energy during the MRI procedure.

Figure 2:
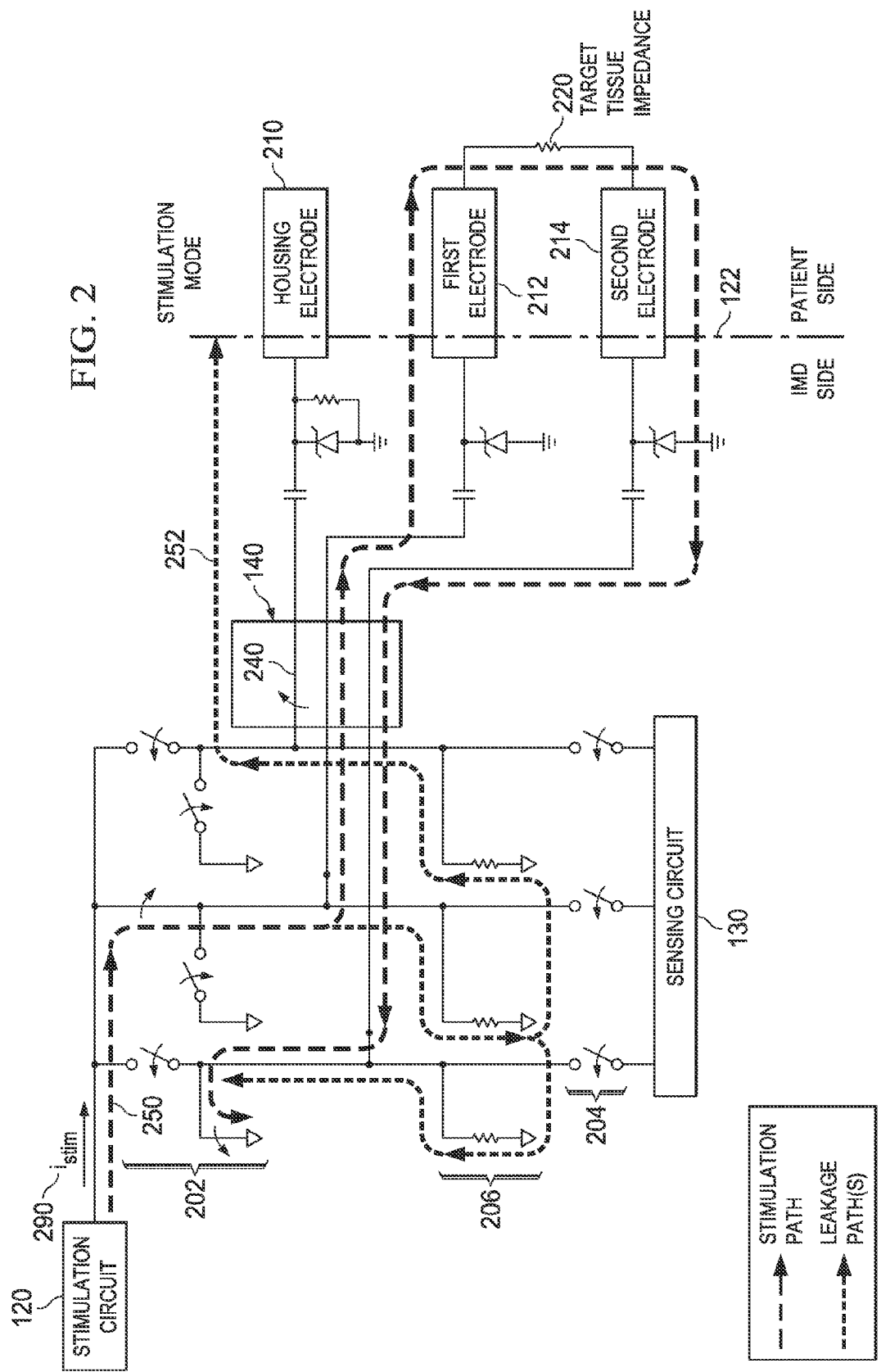
FIG. 2 is a schematic circuit diagram of a first particular embodiment of circuit components of the implantable medical device of FIG. 1 showing current flows during operation in a stimulation mode.

FIG. 2 is a schematic circuit diagram of a first particular embodiment of circuit components of the implantable medical device 110 of FIG. 1 showing current flows in a stimulation mode. For example, FIG. 2 illustrates the stimulation circuit 120, the sensing circuit 130, and an embodiment of the switch matrix 140. The circuit elements illustrated in FIG. 2 may be internal to the housing 122 of the implantable medical device.

FIG. 2 further illustrates electrode connectors including a housing electrode 210, a first electrode 212 and a second electrode 214. The first electrode 212 and the second electrode 214 may be coupled to target tissue of the patient, which may provide a target tissue impedance 220 to a stimulation current 290 (or stimulation signal) from the stimulation circuit 120. The stimulation circuit 120 may be coupled to the electrodes 210-214 via a circuit path that includes one or more switches 202 such as switches within an application specific integrated circuit (ASIC) or within the controller 124 of the implantable medical device 110. The sensing circuit 130 may be selectively coupled to the electrodes 210-214 by one or more switches 204. Additionally, the sensing circuit 130 may be coupled to one or more ground paths 206. In a particular embodiment, the housing 122 is conductive and provides a local ground for the ground paths 206.

FIG. 2 illustrates a particular embodiment of current paths during operation of the implantable medical device 110 in a stimulation mode in which a first switch 240 of the switch matrix 140 is closed. The first switch 240 is coupled to a circuit path between the stimulation circuit 120 and the housing electrode 210. Accordingly, the embodiment illustrated in FIG. 2 illustrates current paths that may occur due to absence of the switch matrix 140 or due to improper configuration of the switch matrix 140 (i.e., closing of the first switch in the stimulation mode). FIG. 2 is shown to contrast the circuit configuration of FIG. 4 in order to facilitate understanding of particular benefits of the switch matrix 140.

When the stimulation circuit 120 applies the stimulation current 290, the stimulation current 290 may flow along a stimulation path 250. The stimulation path 250 routes current through the first electrode 212 and the second electrode 214 via the target tissue of the patient. However, because the ground paths 206 are coupled to the housing, the stimulation current may also flow along one or more leakage paths 252. For example, a leakage path 252 may be present between the housing electrode 210 and one or more of the ground paths 206. Current flowing through the one or more leakage paths 252 may be referred to herein as leakage current. The one or more leakage paths 252 may cause heating of the housing due to current dissipation, or may reduce the stimulation efficacy by diverting current away from the stimulation signal. By opening the first switch 240, as illustrated in FIG. 4, the one or more leakage paths 252 can be mitigated since the ground paths 206 may be electrically coupled to the housing of the implantable medical device.

Figure 3:
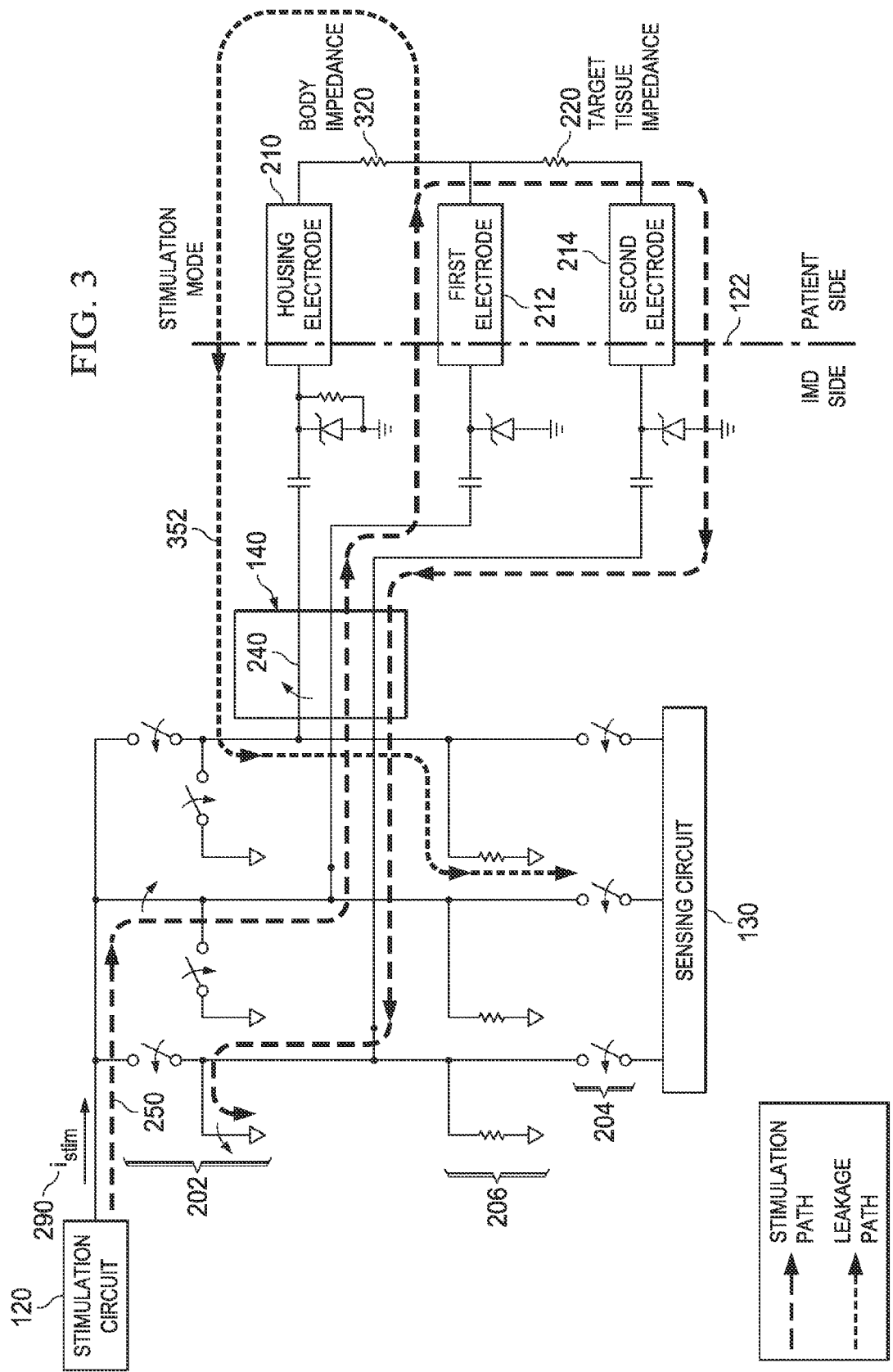
FIG. 3 is a schematic circuit diagram of a second particular embodiment of circuit components of the implantable medical device of FIG. 1 showing current flows during operation in a stimulation mode.

FIG. 3 illustrates a second particular embodiment of current paths during operation of the implantable medical device 110 in a stimulation mode in which the first switch 240 of the switch matrix 140 is closed. In FIG. 3, the stimulation path 250 is identical to the stimulation path 250 of FIG. 2. However, in FIG. 3, a second leakage path 352 is shown. The second leakage path 352 may be present between the first electrode 212 and the housing electrode 210. Although it is not shown in FIG. 3, the second leakage path 352 may also or in the alternative be present between the housing electrode 210 and the second electrode 214.

In the embodiment of FIG. 3, stimulation may be provided to target tissue of the patient, as illustrated by the target tissue impedance 220, and unintended stimulation may be provided to other tissue of the patient, as illustrated by body impedance 320. Thus, improper configuration of the first switch 240 or absence of the first switch 240 may lead to unintended stimulation of non-target body tissue. However, by opening the first switch 240, the switch matrix 140 may prevent or reduce the unintended stimulation caused by the second leakage path 352.

Figure 4:
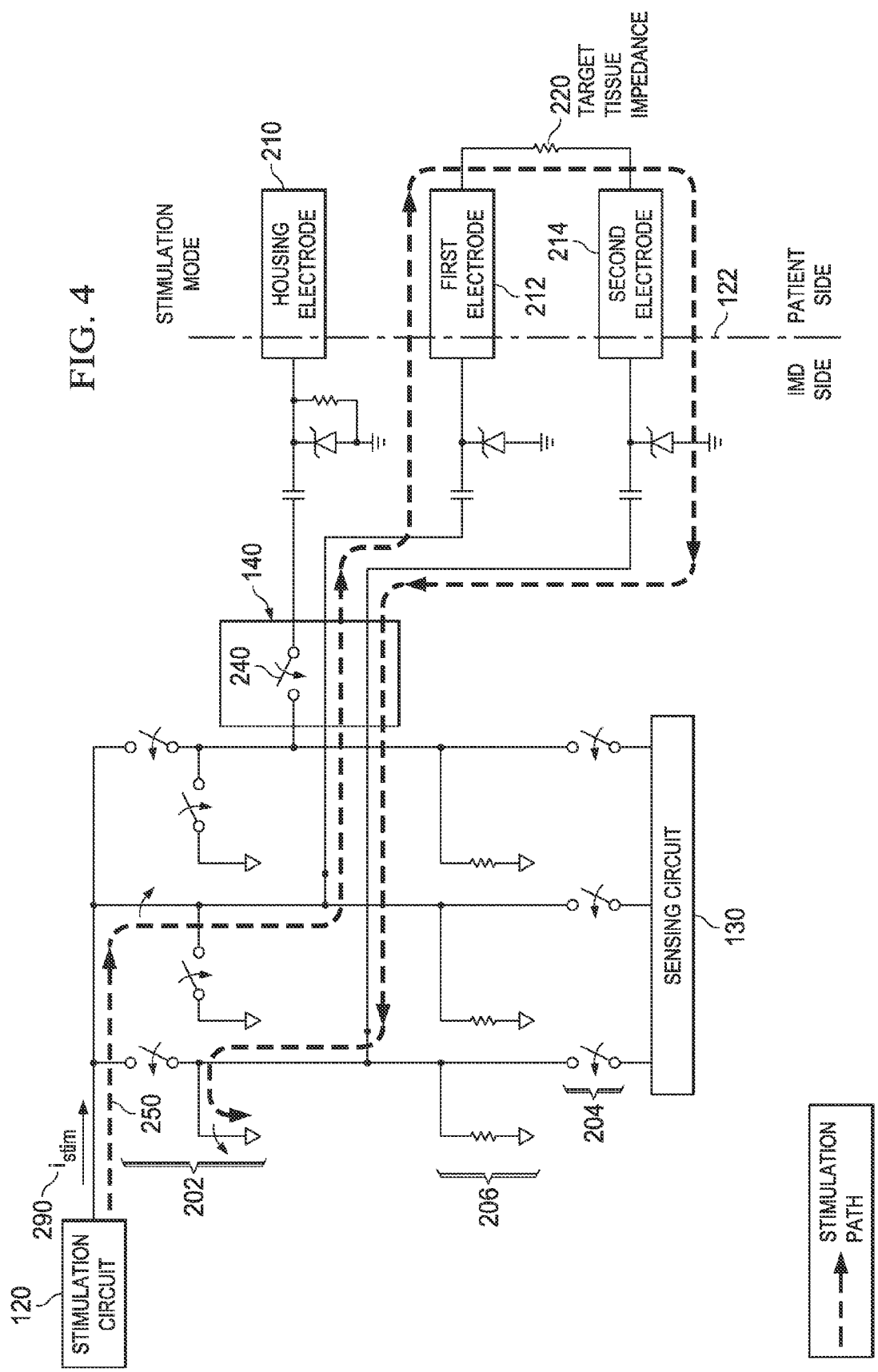
FIG. 4 is a schematic circuit diagram of a third particular embodiment of circuit components of the implantable medical device of FIG. 1 showing current flows during operation in a stimulation mode.

FIG. 4 illustrates a particular embodiment of current paths during operation of the implantable medical device 110 in a stimulation mode of the implantable medical device in which the first switch 240 is open during stimulation. The open first switch 240 prevents or reduces passage of leakage current (e.g., current passing along the leakage path 252 of FIG. 2, the second leakage path 352 of FIG. 3, or both) to the housing electrode 210. Accordingly, in FIG. 4, the stimulation current 290 flows along the stimulation path 250 and no leakage path is shown.

Figure 5:
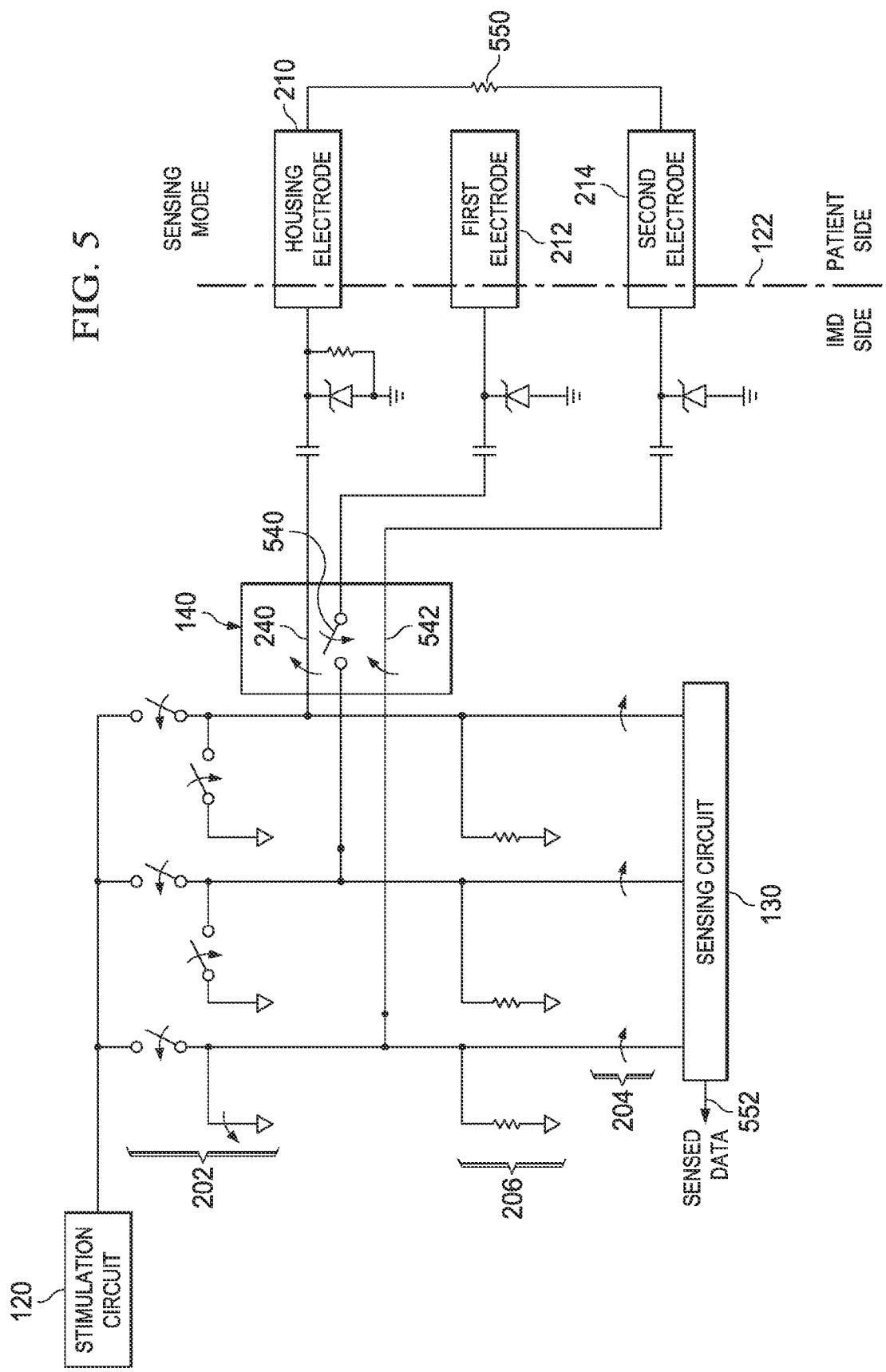
FIG. 5 is a schematic circuit diagram of a particular embodiment of circuit components of the implantable medical device of FIG. 1 during operation in a sensing mode.

FIG. 5 illustrates a particular embodiment of the implantable medical device 110 operating in a sensing mode. In the sensing mode of FIG. 5, one or more switches of the switch matrix 140 may be open. For example, a second switch 540 of the switch matrix 140 may be open. Additionally, two or more other switches of the switch matrix 140 are closed enabling current flow to from the electrodes 210-214 to the sensing circuit 130. For example, the first switch 240 is closed and a third switch 542 is closed. When the first switch 240 is closed, the housing electrode 210 may be electrically coupled to circuitry internal to the implantable medical device (e.g., to be used as a sensing electrode).

The closed first switch 240 and third switch 542 provide a current path from the sensing circuit 130, to the housing electrode 210, through sensed tissue 550 of the patient, and back to the sensing circuit 130 via the second electrode 214. In other embodiments, current may flow in an opposite direction (i.e., from the second electrode 214 to the housing electrode 210), or to one or more different electrodes (e.g., between the housing electrode 210 and the first electrode 212, or between the first electrode 212 and the second electrode 214).

In a particular embodiment, the sensing circuit 130 may generate sensed data 552 in response to the current flow. For example, the sensing circuit 130 may apply current to the internal circuitry of the implantable medical device, and the current may pass through the sensed tissue 550 and return to the sensing circuit 130. The sensing circuit 130 may generate sensed data 552 based on differences between the current applied to the internal circuitry and the return current. Alternatively, one or more of the electrodes 210, 212, and 214 may include (or be coupled to) a sensing device that generates a signal (e.g., a sensing current or sensing voltage) responsive to a body parameter (e.g. a thermocouple device that generates a voltage or current based on a temperature difference within the body; a piezoelectric, capacitive, or microelectromechanical systems device that may vary a parameter than can be monitored (such as capacitance or resistance) or generate a voltage or current responsive to pressure, acceleration, or movement, etc.; an electrochemical device that generates a voltage or current based on presence of a chemical within the body; an accelerometer device that generates a voltage or current based on movement, etc.).

Figure 6:
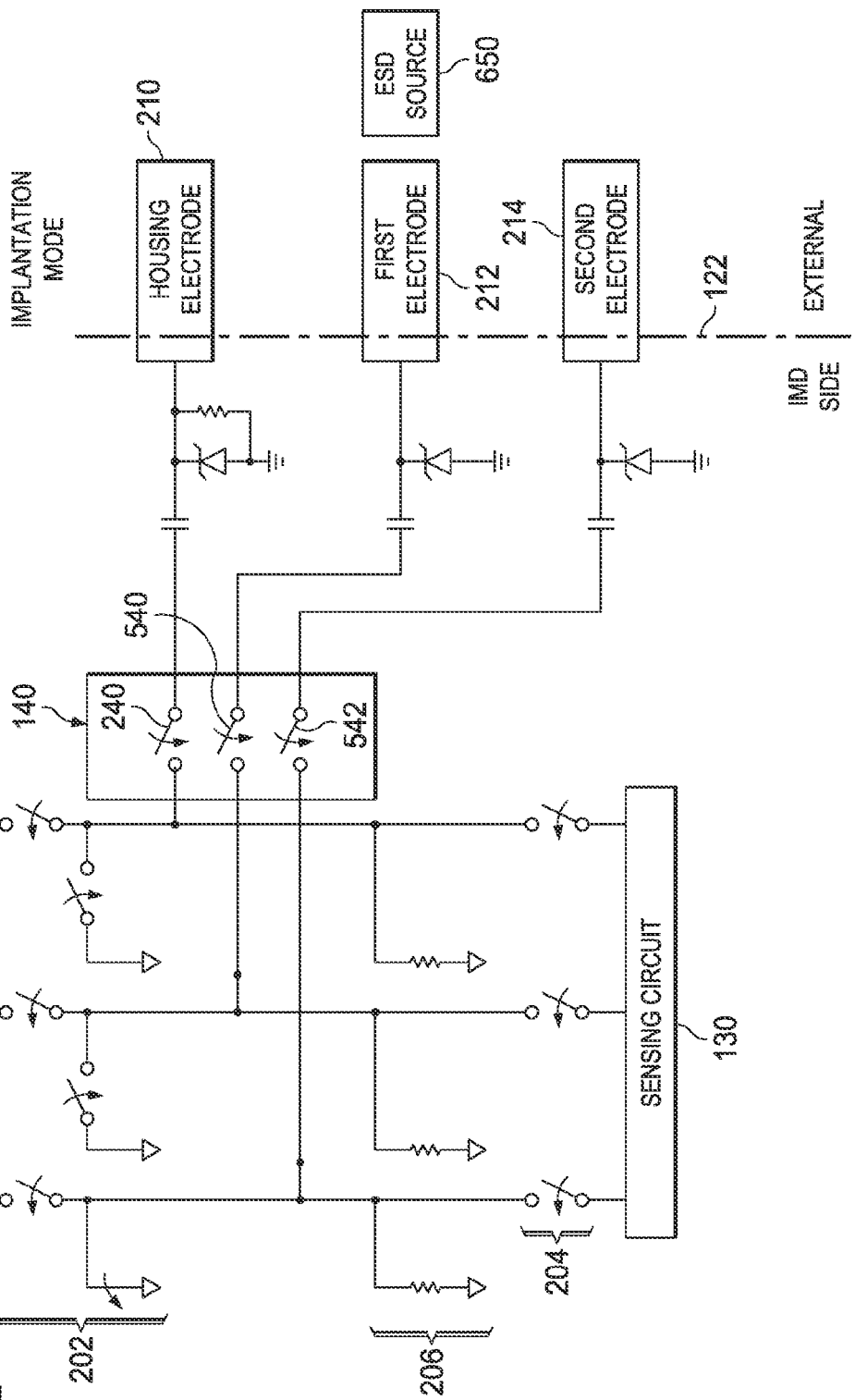
FIG. 6 is a schematic circuit diagram of a particular embodiment of circuit components of the implantable medical device of FIG. 1 during operation in an implantation mode.

FIG. 6 illustrates a particular embodiment of the implantable medical device 110 during operation in an implantation mode. In the implantation mode, each of the switches 240, 540, 542 of the switch matrix 140 is open. Alternatively, the switch matrix 140 may include additional switches and only switches of the switch matrix 140 that are coupled to electrode connectors, such as the housing electrode 210, the first electrode 212, and the second electrode 214 may be opened. Thus, in presence of an electrostatic discharge (ESD) source 650, internal circuit components of the implantable medical device, such as the sensing circuit 130, the stimulation circuit 120, and other circuit components, are electrically isolated by the open switches and may be protected from damage due to electrostatic discharge.

Figure 7:
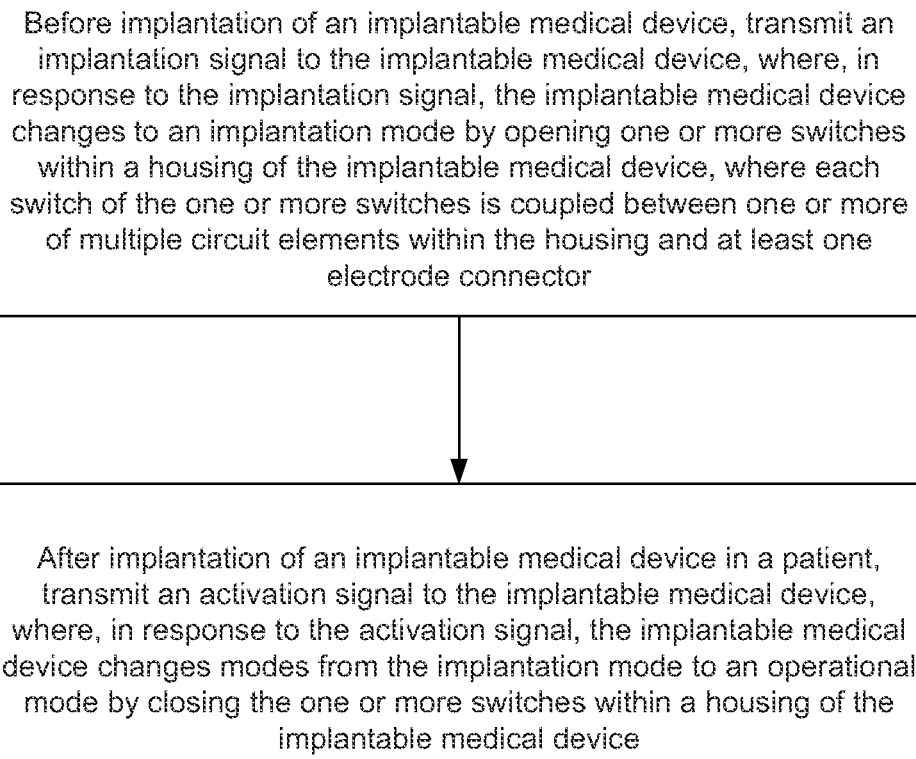
FIG. 7 is a flowchart of a first particular embodiment of a method of operation associated with the implantable medical device of FIG. 1.

FIG. 7 illustrates a particular embodiment of a method 700 of operation associated with an implantable medical device. For example, the method 700 may be performed by the external device 150 of FIG. 1. The method 700 includes, at 702, before implantation of a medical device, (such as the implantable medical device 110 of FIG. 1) transmitting an implantation signal (such as the first signal 160 of FIG. 1) to the implantable medical device. For example, the signal 160 may be transmitted by the transmitter 152 of the external device 150. The signal may include data, a command or another indication that the implantable medical device is to switch to an implantation mode. In response to the implantation signal, the implantable medical device may enter an implantation mode by opening one or more switches within a housing of the implantable medical device. For example, the one or more switches may correspond to one or more switches of the switch matrix 140. Each of the one or more switches may be coupled between one or more circuit elements within the housing and at least one electrode connector.

The method 700 may also include, at 704, after implantation of the implantable medical device (e.g., within a patient), transmitting an activation signal (such as the second signal 162 of FIG. 1) to the implantable medical device. In response to the activation signal, the implantable medical device may change modes from the implantation mode to an operational mode. For example the implantable medical device may close one or more switches within the housing of the implantable medical device. To illustrate, when the operational mode is a stimulation mode, the switch matrix 140 may be configured in the manner illustrated in FIG. 4. Thus, for example, the first switch 240 between the housing electrode 210 and the stimulation circuit 120 may be opened, and one or more other switches may be closed. When the operational mode is a sensing mode, the switch matrix 140 may be configured in the manner illustrated in FIG. 5. Thus, for example, the first switch 240 between the housing electrode 210 and the sensing circuit 130 may be closed.

Figure 8:
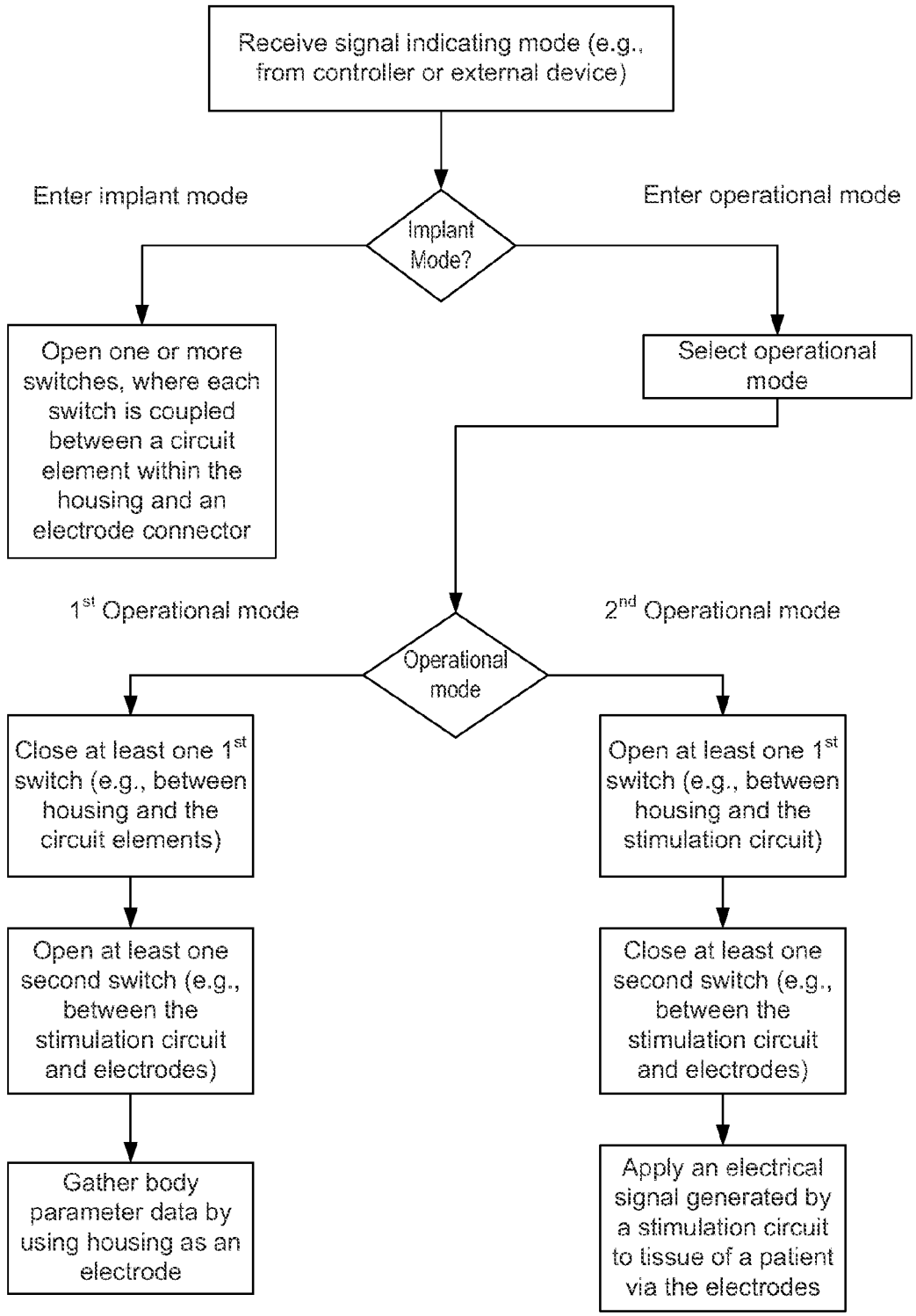
FIG. 8 is a flowchart of a second particular embodiment of a method of operation of the implantable medical device of FIG. 1.

FIG. 8 illustrates a second particular embodiment of a method of operating an implantable medical device. For example, the method 800 may be performed by an implantable medical device, such as the implantable medical device 110 of FIG. 1.

The method 800 includes, at 802, receiving a signal indicating a mode. For example, the signal may include the first signal 160 or the second signal 162 of FIG. 1, which may be received at the receiver 132 from the transmitter 152 of the external device 150. In another example, the signal may be generated internal to the controller 124 of FIG. 1 (e.g., generated by a portion of the controller 124 and received by another portion of the controller 124) in response to an event, such as expiration of a time period, or detection of a particular condition (e.g., detection of a body parameter having a particular value, detection of a charging signal, etc.). The signal may indicate or be associated with a particular mode, such as an implantation mode or a particular operational mode.

The method 800 may also include, at 804, determining whether the signal indicates the implantation mode. When the signal indicates the implantation mode, the implantable medical device may enter the implantation mode. For example, the implantable medical device may open one or more switches, at 806. Each of the one or more switches may be coupled between a circuit element within a housing of the implantable medical device and one or more electrode connectors. For example, the switches may be one or more switches of the switch matrix 140 of FIGS. 1-6.

When the signal indicates an operational mode, the implantable medical device may enter an operational mode. For example, the implantable medical device may select a particular operational mode (e.g., a stimulation mode or a sensing mode), at 808. When the selected operational mode is a first operational mode, at 810, such as a sensing mode, the implantable medical device may close at least one switch between the housing of the implantable medical device and one or more circuit elements, at 812. Additionally or alternatively, the implantable medical device may open at least one second switch, such as one or more switches between a stimulation circuit and one or more electrodes, at 814. For example, the implantable medical device may configure switches of the switch matrix 140 as illustrated in FIG. 5. The method 800 may also include, at 812, gathering body parameter data by using the housing as an electrode. For example, the sensing circuit 130 of FIGS. 1-6 may gather body parameter data. The body parameter data may be stored in a memory of the implantable medical device, transmitted to an external device, or both. Additionally or alternatively, the body parameter data may be processed by the implantable medical device to determine processed body parameter data, which may be stored in the memory of the implantable medical device, transmitted to the external device, or both.

At 810, when the operational mode is a second operational mode, such as a stimulation mode, the implantable medical device may open at least one switch between the housing and a stimulation circuit, at 820. Alternatively or in addition, the implantable medical device may close at least one second switch, such as a switch between the stimulation circuit and the one or more electrodes, at 822. For example, the implantable medical device may configure switches of the switch matrix 140 as illustrated in FIG. 4. The method 800 may also include applying an electrical signal generated by the stimulation circuit to tissue of the patient via the electrodes, at 824.

Embodiments disclosed herein provide electrostatic discharge protection to the implantable medical device reducing risk of damage from the electrostatic discharge during implantation of the implantable medical device. Further, the switch matrix may provide leakage current protection. The leakage current protection may reduce a risk of unintended current flow to non targeted tissue of a patient's body. Further, the leakage current protection may reduce a risk of damage to circuitry of the implantable medical device. The leakage current protection may also reduce charge buildup on the electrodes and/or housing which may improve efficacy and accuracy of sensing.

The illustrations of the embodiments described herein are intended to provide a general understanding of the structure of the various embodiments. The illustrations are not intended to serve as a complete description of all of the elements and features of apparatus and systems that utilize the structures or methods described herein. Many other embodiments may be apparent to those of skill in the art upon reviewing the disclosure. Other embodiments may be utilized and derived from the disclosure, such that structural and logical substitutions and changes may be made without departing from the scope of the disclosure. For example, method steps may be performed in a different order than is shown in the figures or one or more method steps may be omitted. Accordingly, the disclosure and the figures are to be regarded as illustrative rather than restrictive.

Moreover, although specific embodiments have been illustrated and described herein, it should be appreciated that any subsequent arrangement designed to achieve the same or similar results may be substituted for the specific embodiments shown. This disclosure is intended to cover any and all subsequent adaptations or variations of various embodiments. Combinations of the above embodiments, and other embodiments not specifically described herein, will be apparent to those of skill in the art upon reviewing the description.

The Abstract of the Disclosure is submitted with the understanding that it will not be used to interpret or limit the scope or meaning of the claims. In addition, in the foregoing Detailed Description, various features may be grouped together or described in a single embodiment for the purpose of streamlining the disclosure. This disclosure is not to be interpreted as reflecting an intention that the claimed embodiments require more features than are expressly recited in each claim. Rather, as the following claims reflect, the claimed subject matter may be directed to less than all of the features of any of the disclosed embodiments.

What is claimed is:

1. An implantable medical device comprising:
   a housing;
   multiple electrode connectors;
   multiple circuit elements within the housing; and
   a switch matrix within the housing, wherein the switch matrix comprises multiple switches, wherein each switch of the multiple switches corresponds to a different electrode connector of the multiple electrode connectors, and wherein, in an implantation mode, the multiple switches of the switch matrix are open to isolate the multiple circuit elements from the multiple electrode connectors.

2. The implantable medical device of claim 1, further comprising a receiver within the housing, wherein a position of each of the multiple switches is remotely controllable in response to a signal received via the receiver.

3. The implantable medical device of claim 1, wherein the implantable medical device has a plurality of operational modes, wherein a position of at least one switch of the switch matrix is changed when the implantable medical device changes from a first operational mode to a second operational mode, and wherein the plurality of operational modes comprises:
   a charging mode, wherein one or more switches of the switch matrix are closed to enable charging a power supply of the implantable medical device;
   a magnetic resonance imaging mode, wherein the magnetic resonance imaging mode is enabled in response to a user input, a change in magnetic field at the implantable medical device, detection of high power electromagnetic energy during a magnetic resonance imaging procedure, or a combination thereof; and
   the implantation mode.

4. The implantable medical device of claim 1, wherein, in a first operational mode, the housing is used as an electrode, and wherein the switch matrix includes a first switch coupled between the housing and one or more of the multiple circuit elements.

5. The implantable medical device of claim 4, further comprising a stimulation circuit, wherein a second operational mode is a stimulation mode in which an electrical signal generated by the stimulation circuit is applied to tissue of a patient via at least one electrode coupled to the multiple electrode connectors, and wherein the first switch of the switch matrix is open in the stimulation mode to electrically isolate the housing from the stimulation circuit.

6. The implantable medical device of claim 5, further comprising a sensing circuit, wherein the first operational mode is a sensing mode, and wherein the first switch is closed in the sensing mode to electrically couple the housing to the sensing circuit.

7. The implantable medical device of claim 1, further comprising a controller within the housing and coupled to at least one switch of the multiple switches of the switch matrix, wherein a position of the at least one switch is controllable in response to a signal from the controller.

8. The implantable medical device of claim 1, wherein, in at least one operational mode, current is applied from a circuit element of the multiple circuit elements within the housing to at least one electrode connector of the multiple electrode connectors and at least one switch of the multiple switches of the switch matrix is open to reduce leakage current to at least one other electrode of the multiple electrode connectors.

9. The implantable medical device of claim 1, wherein the switch matrix is a single component.

10. The implantable medical device of claim 1, wherein the switch matrix includes:
    a plurality of circuit element terminals; and
    a plurality of electrode terminals,
    wherein a first circuit element terminal of the plurality of circuit element terminals is coupled to a first switch of the multiple switches and one or more circuit elements of the multiple circuit elements,
    wherein a first electrode terminal of the plurality of electrode terminals is coupled to the first switch and to a first electrode connector of the multiple electrode connectors,
    wherein a second circuit element terminal of the plurality of circuit element terminals is coupled to a second switch of the multiple switches,
    wherein a second electrode terminal of the plurality of electrode terminals is coupled to the second switch and to a second electrode connector of the multiple electrode connectors,
    wherein a number of the plurality of electrode terminals corresponds to a number of the multiple electrode connectors; and
    wherein, in the implantation mode, the first electrode connector is isolated from the second electrode connector.

11. The implantable medical device of claim 1, further comprising a sensing device configured to generate a signal responsive to a body parameter, wherein the signal comprises a sensing current, a sensing voltage, or a combination thereof, and wherein the body parameter comprises pressure, acceleration, movement, presence of a particular chemical, or any combination thereof.

12. A method comprising:
    after implantation of an implantable medical device in a patient while the implantable medical device is in an implantation mode, transmitting an activation signal to the implantable medical device; and in response to the activation signal, sending a signal to the implantable medical device to change modes of the implantable medical device from the implantation mode to an operational mode by closing one or more switches of multiple switches of a switch matrix within a housing of the implantable medical device, wherein the switch matrix is coupled between one or more of multiple circuit elements within the housing and multiple electrode connectors, wherein each switch of the multiple switches corresponds to a different electrode connector of the multiple electrode connectors, and wherein when the implantable medical device is in the implantation mode, the one or more switches of the switch matrix are open to isolate the multiple circuit elements from the multiple electrode connectors.

13. The method of claim 12, further comprising, before implantation of the implantable medical device, transmitting an implantation signal to the implantable medical device, wherein, in response to the implantation signal, the implantable medical device changes to the implantation mode by opening one or more switches of the multiple switches of the switch matrix within the housing of the implantable medical device.

14. The method of claim 12, wherein the operational mode includes a sensing mode, wherein, in the sensing mode, the housing is used as an electrode, at least one of the multiple switches of the switch matrix is closed to provide a conduction path from the housing to a sensing circuit within the housing, and at least one other switch of the multiple switches of the switch matrix is open to electrically isolate a particular electrode connector from the sensing circuit.

15. The method of claim 12, wherein the operational mode includes a stimulation mode, wherein, in the stimulation mode, a particular switch of the switch matrix that is between the housing and a sensing circuit is open.

16. The method of claim 12, wherein the operational mode includes a stimulation mode, wherein, in the stimulation mode, a particular switch of the multiple switches of the switch matrix between a particular electrode of the implantable medical device and a stimulation circuit is closed.

17. The method of claim 16, wherein, in the stimulation mode, one or more other switches of the switch matrix coupled to the housing are open.

18. The method of claim 12, wherein, in at least one operational mode, at least one switch of the multiple switches of the switch matrix is open to reduce a leakage current to at least one electrode connector of the multiple electrode connectors.

19. A method comprising:

during a first operational mode of an implantable medical device:

closing a first switch of a switch matrix, wherein the switch matrix is located in a circuit path between a housing of the implantable medical device and one or more circuit elements within the implantable medical device; and gathering body parameter data by using the housing as an electrode;

during a second operational mode of the implantable medical device:

opening the first switch; and applying an electrical signal generated by a stimulation circuit of the implantable medical device to tissue of a patient via electrodes coupled to the stimulation circuit via multiple electrode connectors; and during an implantation mode of the implantable medical device:

opening a set of multiple switches of the switch matrix, wherein each switch of the set of multiple switches corresponds to an electrode connector of the multiple electrode connectors, and wherein opening the set of multiple switches electrically isolates the one or more circuit elements within the implantable medical device from the multiple electrode connectors and the housing.

20. The method of claim 19, further comprising:

opening at least one second switch of the switch matrix during the first operational mode; and closing the at least one second switch during the second operational mode.

* * * * *